(12) United States Patent
Burkholz et al.

(10) Patent No.: US 12,070,563 B2
(45) Date of Patent: *Aug. 27, 2024

(54) PERIPHERAL INTRAVENOUS CATHETER WITH WINGED GRIP

(71) Applicant: Becton, Dickinson and Company, Franklin Lakes, NJ (US)

(72) Inventors: Jonathan Karl Burkholz, Salt Lake City, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 161 days.

This patent is subject to a terminal disclaimer.

(21) Appl. No.: 16/553,560

(22) Filed: Aug. 28, 2019

(65) Prior Publication Data

US 2019/0381283 A1 Dec. 19, 2019

Related U.S. Application Data

(62) Division of application No. 15/625,079, filed on Jun. 16, 2017, now Pat. No. 10,434,286, which is a division of application No. 14/326,087, filed on Jul. 8, 2014, now abandoned.

(51) Int. Cl.
*A61M 25/06* (2006.01)
*A61M 25/00* (2006.01)

(52) U.S. Cl.
CPC ........ *A61M 25/0637* (2013.01); *A61M 25/06* (2013.01); *A61M 25/0606* (2013.01); *A61M 25/0612* (2013.01); *A61M 25/0625* (2013.01); *A61M 25/0693* (2013.01); *A61M 2025/0008* (2013.01)

(58) Field of Classification Search
CPC ................ A61M 25/06; A61M 25/062; A61M 25/0693; A61M 25/0606; A61M 25/0625; A61M 25/0637; A61M 2025/0008; A61M 25/0612; A61M 25/0075; A61M 39/06
See application file for complete search history.

(56) References Cited

U.S. PATENT DOCUMENTS

| | | | |
|---|---|---|---|
| 4,275,729 A | 6/1981 | Silver et al. |
| 4,592,746 A | 6/1986 | Burkholder et al. |
| 5,156,596 A | 10/1992 | Balbierz et al. |
| (Continued) | | | |

FOREIGN PATENT DOCUMENTS

| | | |
|---|---|---|
| EP | 0332884 | 2/1989 |
| EP | 0545671 | 3/1999 |
| (Continued) | | |

*Primary Examiner* — Tiffany Legette
(74) *Attorney, Agent, or Firm* — Kirton McConkie; Whitney Blair; Kevin Stinger

(57) ABSTRACT

A PIVC includes a catheter adapter having a catheter that extends distally from the catheter adapter, and an introducer needle that inserts through the catheter. The introducer needle has a grip component at a proximal end of the introducer needle. The grip component extends outwardly and distally to form a winged grip adjacent the catheter adapter when the introducer needle is inserted within the catheter. The grip component can be rotatable within the catheter adapter to allow repositioning of the winged grip with respect to the catheter adapter.

5 Claims, 11 Drawing Sheets

(56) References Cited

U.S. PATENT DOCUMENTS

| | | | |
|---|---|---|---|
| 5,391,152 A * | 2/1995 | Patterson | A61M 25/0097 604/165.04 |
| 5,554,127 A | 9/1996 | Crouther et al. | |
| 5,676,656 A | 10/1997 | Brimhall | |
| 2001/0041871 A1 * | 11/2001 | Brimhall | A61M 25/0637 604/167.02 |
| 2002/0128604 A1 | 9/2002 | Nakajima | |
| 2003/0078540 A1 * | 4/2003 | Saulenas | A61M 25/0631 604/110 |
| 2003/0212372 A1 * | 11/2003 | Bills | B05C 17/00593 604/236 |
| 2004/0225261 A1 | 11/2004 | Millerd | |
| 2007/0010796 A1 | 1/2007 | Moran et al. | |
| 2007/0038188 A1 * | 2/2007 | Bialecki | A61M 25/0618 604/164.08 |
| 2007/0270758 A1 | 11/2007 | Hanner et al. | |
| 2008/0208132 A1 | 8/2008 | Funamura et al. | |
| 2011/0009717 A1 * | 1/2011 | Davis | A61B 5/150389 600/309 |
| 2013/0150793 A1 | 6/2013 | Beissel et al. | |

FOREIGN PATENT DOCUMENTS

| | | |
|---|---|---|
| EP | 0732120 | 5/2003 |
| EP | 2077133 | 7/2009 |
| JP | 07-185002 | 7/1995 |
| JP | 08-257129 | 10/1996 |
| JP | 08-257130 | 10/1996 |
| JP | 2001-517502 | 10/2001 |
| JP | 2003-180829 | 7/2003 |
| JP | 2013-535997 | 9/2013 |
| WO | 00/12171 | 3/2000 |
| WO | 2008/000148 | 1/2008 |
| WO | 2009/129290 | 10/2009 |
| WO | 2010/111285 | 9/2010 |

* cited by examiner

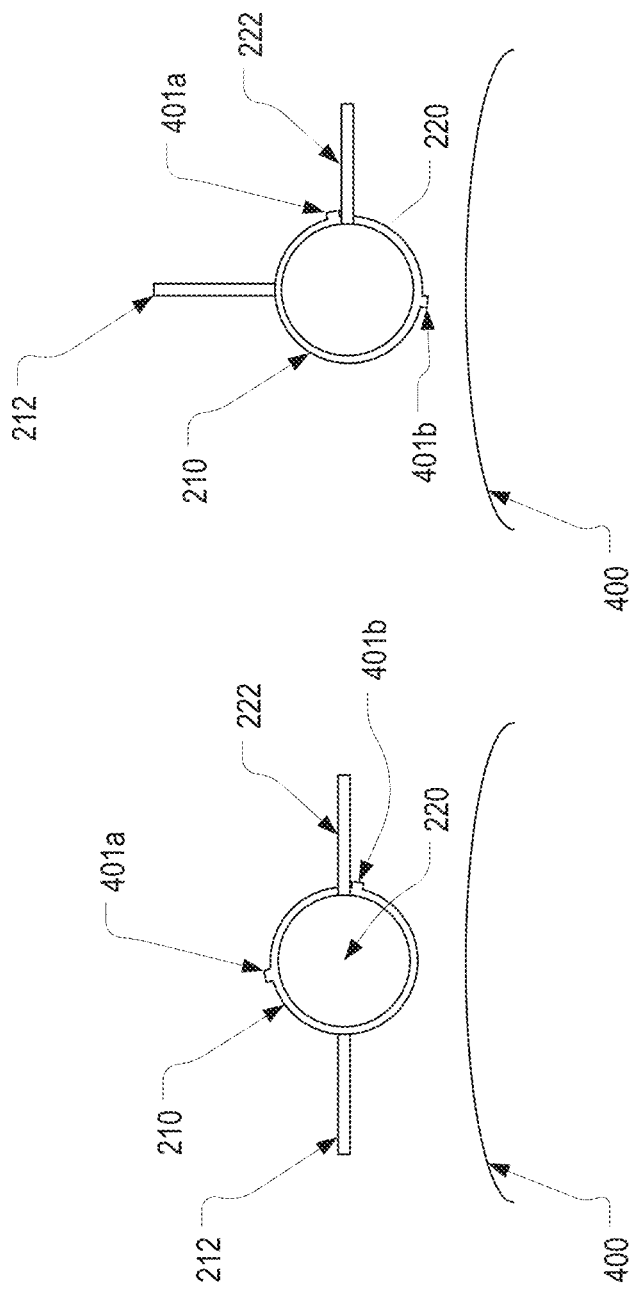

PERIPHERAL INTRAVENOUS CATHETER WITH WINGED GRIP

CROSS-REFERENCE TO RELATED APPLICATIONS

This application is a divisional of U.S. application Ser. No. 15/625,079, filed Jun. 16, 2017, titled PERIPHERAL INTRAVENOUS CATHETER WITH WINGED GRIP, which is a divisional of U.S. application Ser. No. 14/326,087, filed Jul. 8, 2014, titled PERIPHERAL INTRAVENOUS CATHETER WITH WINGED GRIP, which is incorporated herein in its entirety.

BACKGROUND OF THE INVENTION

The present invention relates generally to non-integrated peripheral intravenous catheters. More particularly, the present invention is directed to non-integrated peripheral intravenous catheters that include a winged grip.

A winged infusion set is a device that is commonly used to access a peripheral vein either for intravenous injection or for blood draw. An example of a winged infusion set 700 is shown in FIG. 7. Winged infusion set 700 comprises a needle 701, wings 702 within which needle 701 is positioned, and extension tubing 703 that is connected to a proximal end of needle 701. A proximal end of extension tubing 703 may include an adapter 704 or other structure for connecting another device (e.g. a vacuum tube or a syringe) to winged infusion set 700.

Winged infusion set 700 is an example of an integrated intravenous device. Integrated refers to the fact that extension tubing 703 is integrated with (or is not removed from) needle 701. In winged infusion set 700, needle 701 also remains within the patient's vasculature throughout the use of winged infusion set 700. In other words, needle 701 functions as a catheter through which fluids are injected into the patient's vasculature and/or blood is withdrawn from the patient's vasculature.

Wings 702 provide a gripping surface during insertion of needle 701. Typically, the clinician will grasp wings 702 between a thumb and forefinger which facilitates insertion of needle 701 at a shallow angle. For this reason, a winged infusion set is oftentimes preferred by clinicians when accessing a peripheral vein.

The integrated nature of winged infusion set 700 also minimizes the risk of blood exposure during vascular access. Because needle 701 remains within the patient's vasculature and because extension tubing 703 is connected to needle 701, there is little possibility for blood to escape from winged infusion set 700 (other than through the intended exit point at the proximal end of extension tubing 703).

Winged infusion sets, however, have various disadvantages when compared to other peripheral intravenous devices such as a non-integrated peripheral intravenous catheter. For example, needle 701 is typically made of steel which is more likely to cause vein damage than polymeric catheters. In particular, the sharpened tip of needle 701 may cut, scrape, rupture, or otherwise damage the vein wall while needle 701 is inserted intravenously. For this reason, winged infusion sets are not typically left within the patient for extended periods of time. As a result, if the patient requires multiple vasculature accesses, the patient will likely have to be punctured multiple times since needle 701 is typically not left within the vasculature between accesses.

BRIEF SUMMARY OF THE INVENTION

The present invention extends to non-integrated peripheral intravenous catheters (PIVCs) that include a winged grip. The winged grip PIVCs can be used in a similar manner as integrated winged infusion sets while providing the benefit of an over-the-needle catheter. The winged grip PIVCs, in some embodiments, can also provide blood control features to minimize the risk of exposure to blood. In this way, clinicians that are accustomed to using integrated winged infusion sets can transition to using non-integrated PIVCs without the concern of an increased risk to blood exposure.

The blood control features, in some embodiments, can be configured to allow multiple accesses to the patient's vasculature thereby enabling a winged grip PIVC to be left within the patient's vasculature for longer periods of time and across multiple accesses. In some embodiments, the winged grip can be adjustable while retaining a fixed orientation of the needle bevel to the clinician's grip.

In some embodiments, at least a portion of the winged grip can be formed as part of the introducer needle. For example, a grip component can extend outwardly from the introducer needle to form a winged grip. In some embodiments, the grip component can also function to secure the introducer needle to the catheter adapter of the PIVC.

In a first example embodiment, the present invention is implemented as a PIVC that comprises a catheter adapter having a catheter that extends distally from the catheter adapter, and an introducer needle that inserts through the catheter. The introducer needle has a grip component at a proximal end of the introducer needle. The grip component extends outwardly and distally to form a winged grip adjacent the catheter adapter when the introducer needle is inserted within the catheter.

In the first example embodiment, the catheter adapter can include a winged grip that extends outwardly from the catheter adapter. The catheter adapter can also include a blood-control feature for preventing blood from flowing proximally through the catheter adapter. The blood-control feature can be configured in some cases to be actuated multiple times to allow blood to flow proximally through the catheter adapter.

In the first example embodiment, the grip component can secure the introducer needle to the catheter adapter. In some cases, the grip component can be rotatable within the catheter adapter to allow the repositioning of the winged grip relative to the catheter adapter. In some cases, the introducer needle can include a needle shield for shielding a tip of the introducer needle.

In a second example embodiment, the present invention is implemented as a PIVC that comprises a catheter adapter having a catheter extending distally from the catheter adapter. The catheter adapter includes a first winged grip that extends outwardly from the catheter adapter. The PIVC also comprises an introducer needle that extends through the catheter. The introducer needle includes a grip component positioned at a proximal end of the introducer needle. The grip component forms a second winged grip.

In the second example embodiment, the grip component can secure the introducer needle within the catheter adapter including, in some cases, being rotatable within the catheter adapter thereby allowing the first winged grip to be repositioned with respect to the second winged grip. In some cases, the grip component may also include a vent for venting gases contained within a lumen of the introducer needle. The catheter adapter may also include a blood-control feature for preventing blood from flowing proximally through the catheter adapter.

In a third example embodiment, the present invention is implemented as a PIVC comprising a catheter adapter having a catheter extending distally from the catheter adapter, and an introducer needle that extends through the catheter. The introducer needle includes a grip component positioned at a proximal end of the introducer needle. The grip component secures the introducer needle to the catheter adapter and forms a winged grip that extends outwardly from the introducer needle.

In the third example embodiment, the winged grip can extend distally along the introducer needle such that the winged grip extends alongside the catheter adapter when the introducer needle is secured to the catheter adapter. The grip component can be rotatable within the catheter adapter to enable repositioning of the winged grip around a portion of the catheter adapter. The catheter adapter may also include a winged grip.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 4C and 4D illustrate a variation of the PIVC shown in FIGS. 4A and 4B in which the catheter adapter includes protrusions to limit rotation between the winged grips;

DETAILED DESCRIPTION OF THE INVENTION

Figure 1:
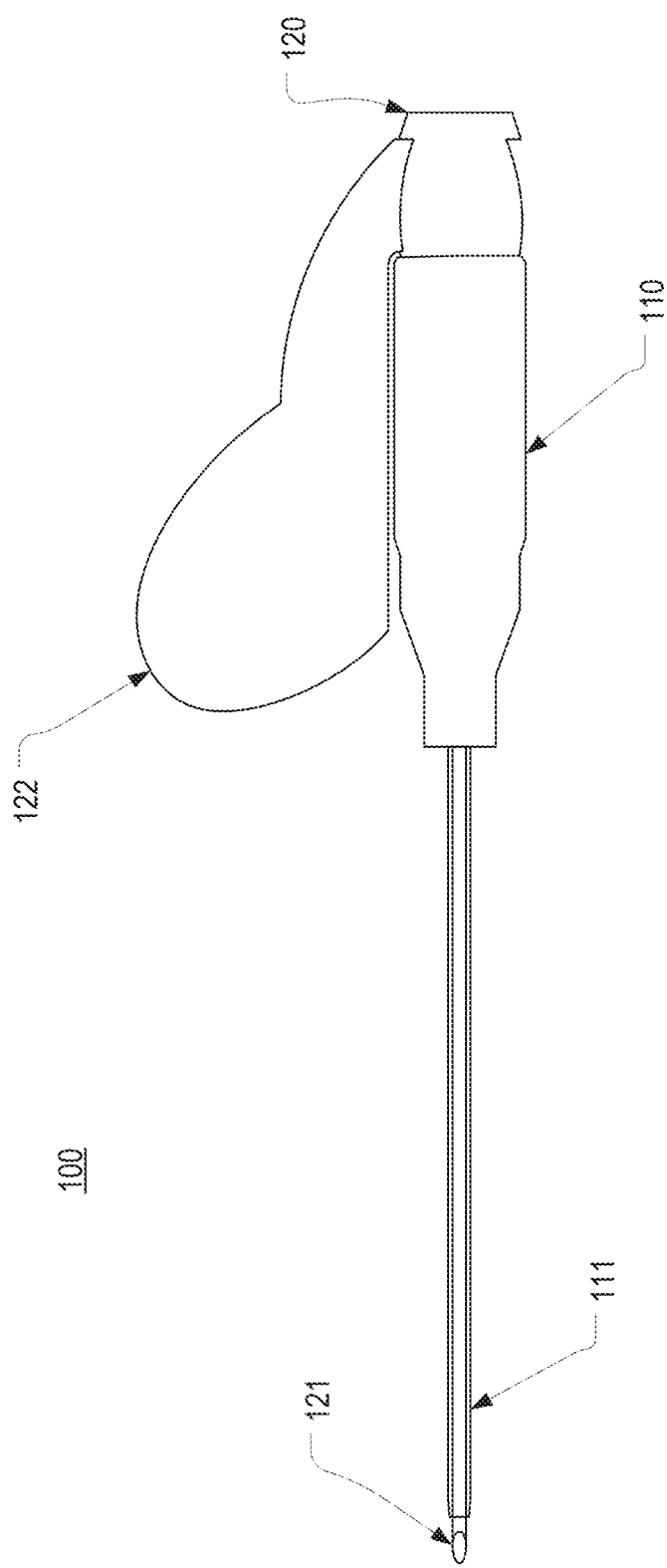
FIG. 1 is a top view of an example PIVC that includes a catheter adapter and an introducer needle having a grip component that forms a winged grip.

FIG. 1 illustrates an example PIVC 100 that is configured in accordance with one or more embodiments of the invention. PIVC 100 includes a catheter adapter 110 and an introducer needle 121. Catheter adapter 110 includes a catheter 111 that extends distally from the catheter adapter. Introducer needle 121 includes a grip component 120 within which introducer needle 121 is secured and from which introducer needle 121 extends distally.

When introducer needle 121 is inserted through catheter 111 (which would be the case prior to inserting catheter 111 into a patient's vasculature), grip component 120 is positioned at a proximal end of catheter adapter 110 as is shown in FIG. 1.

Grip component 120 includes or forms a winged grip 122. Winged grip 122 comprises a portion of grip component 120 (whether integrally or separately formed from grip component 120) that extends distally along and outwardly from catheter adapter 120 when grip component 120 is positioned at the proximal end of catheter adapter 110. In this way, winged grip 122 forms a surface that a clinician can grip while inserting introducer needle 121 into a patient's vasculature.

Figure 1A:
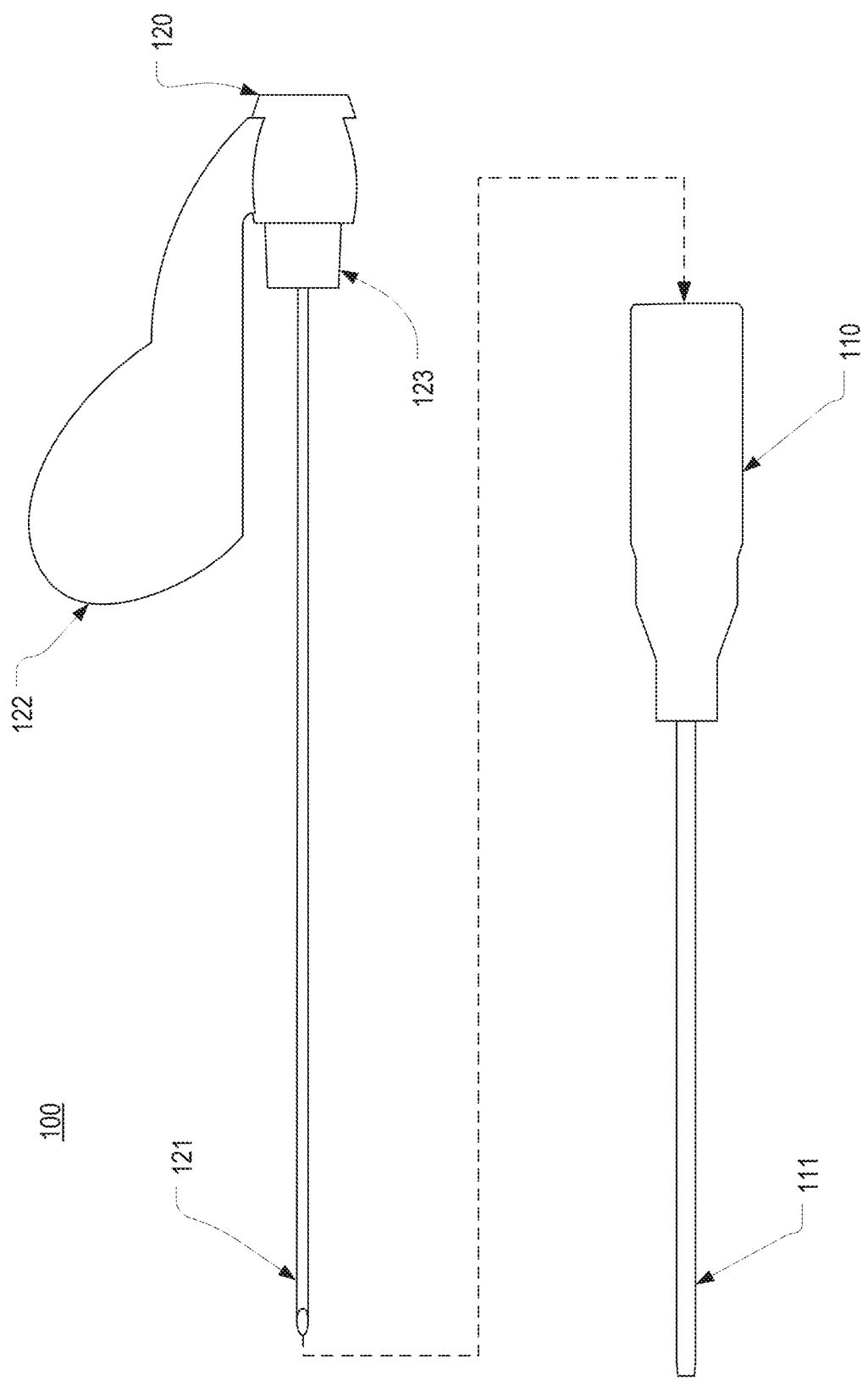
FIG. 1A is an exploded view of the example PIVC of FIG. 1 showing the introducer needle removed from the catheter adapter.

FIG. 1A illustrates an exploded view of PIVC 100 showing introducer needle 121 removed from catheter adapter 110. Once catheter 111 is placed intravenously, introducer needle 121 can be withdrawn from catheter adapter 110 as shown by pulling proximally on grip component 120.

Grip component 120 can include a distal portion 123 that is sized and shaped to be inserted within the proximal end of catheter adapter 110. In some embodiments, distal portion 123 can be circular and have a relatively smooth outer surface thereby allowing grip component 120 to be freely rotated within the proximal opening of catheter adapter 110. In such embodiments, the diameter of distal portion 123 can be slightly larger than the diameter of the proximal opening of catheter adapter 110 so that grip component 120 can be secured to catheter adapter 110. However, in other embodiments, distal portion 123 need not be configured to secure grip component 120 to catheter 110. In such cases, the friction between introducer needle 121 and catheter 111 may be sufficient to prevent introducer needle 121 from separating unintentionally from catheter adapter 110.

In other embodiments, distal portion 123 (as well as an inner surface of catheter adapter 110) can include threads or other structure for securing grip component 120 within catheter adapter 110. In such embodiments, the threads or other structure may also be configured to limit the rotation of grip component 120 within catheter adapter 110. Limiting the rotation of grip component 120 within catheter adapter 110 can facilitate proper positioning of winged grip 122 as will be further described below.

Figure 2:
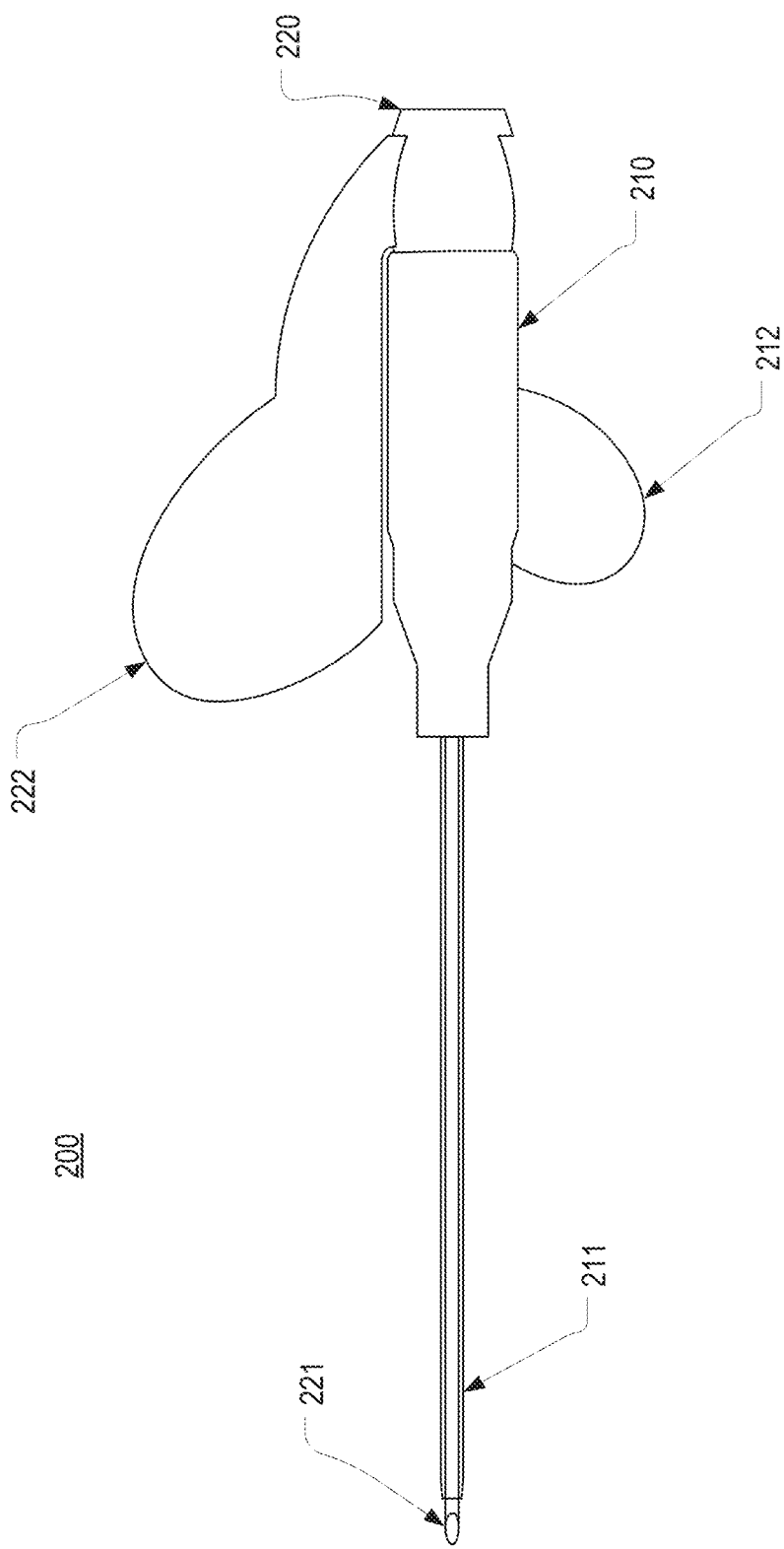
FIG. 2 is a top view of another example PIVC that includes a catheter adapter having a winged grip and an introducer needle having a grip component that forms a winged grip.

FIG. 2 illustrates another example PIVC 200 that is configured in accordance with one or more embodiments of the invention. Similar to PIVC 100, PIVC 200 includes a catheter adapter 210 having a catheter 211 and an introducer needle 221 having a grip component 220 that forms winged grip 222. However, in contrast to PIVC 100, catheter adapter 210 also includes a winged grip 212. Winged grip 212 extends outwardly from catheter adapter 210. In some embodiments, winged grip 212 can be rigid, while in others, winged grip 212 may be flexible or incorporate a hinge to allow movement of winged grip 212 with respect to catheter adapter 210.

Figure 2A:
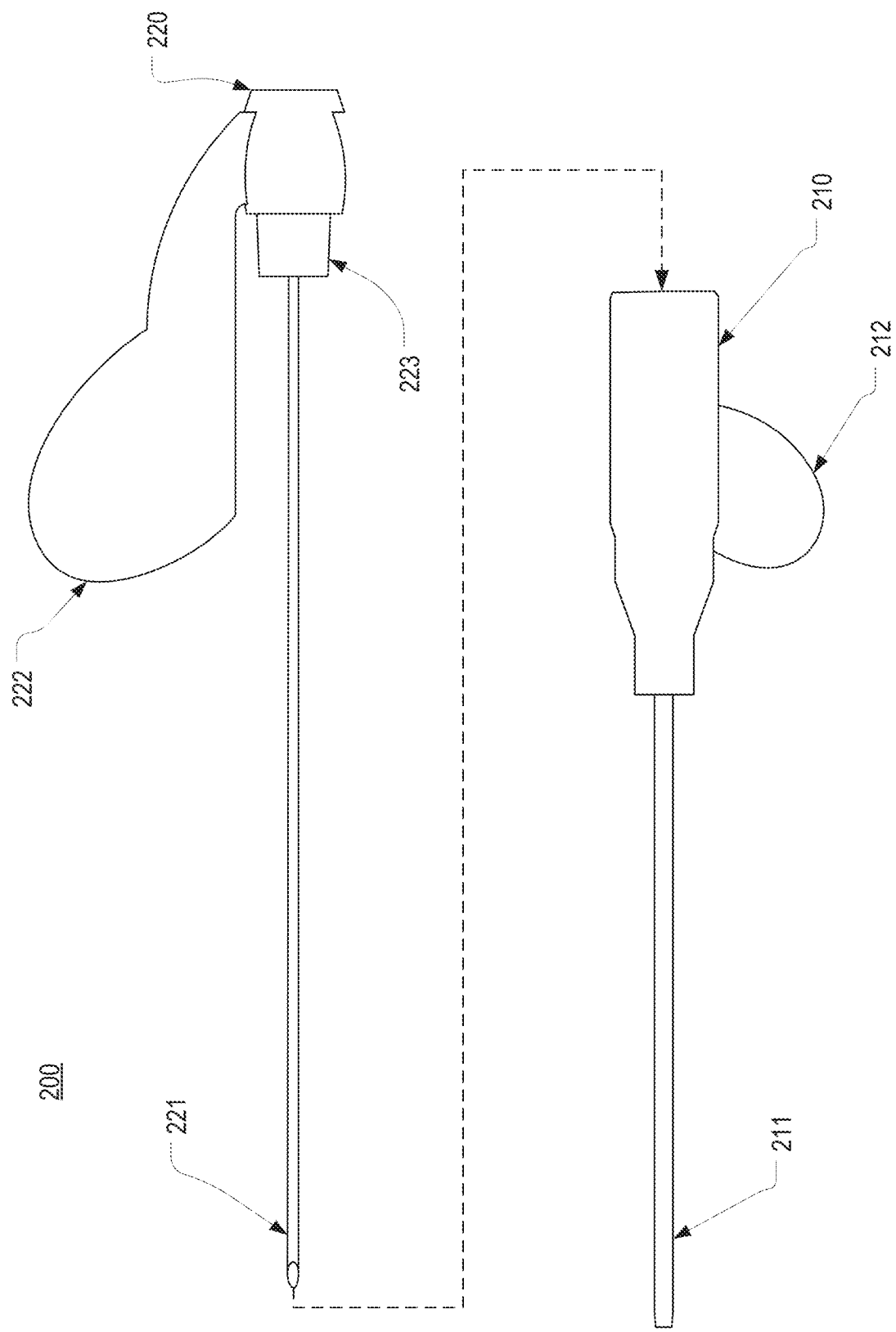
FIG. 2A is an exploded view of the example PIVC of FIG. 2 showing the introducer needle removed from the catheter adapter.

As shown in FIG. 2A, introducer needle 221 can be removed from catheter adapter 210 as described with respect to FIG. 1A above. Grip component 220 can include a distal portion 223 that can be configured in any of the ways described above with respect to distal portion 123.

As shown in each of FIGS. 1, 1A, 2, and 2A, winged grip 122 and 222 can be positioned so that the sharpened or beveled distal tip of the introducer needle and the winged grip have the same orientation. For example, in these figures, winged grip 122 and 222 are positioned so that when the top surface of the winged grip is facing upwards, the beveled distal tip will also face upward. In this way, the clinician can know that the beveled distal tip is in the proper orientation for insertion through the patient's skin when the winged grip of the introducer needle is facing upwards.

Introducer needles 121 and 221 are configured for insertion using the right hand. In particular, the clinician would typically grasp PIVC 100 and 200 in the right hand with the thumb placed on the top surface of winged grip 122/222 and the fingers wrapped underneath winged grip 122/22 and/or catheter adapter 110/210. To configure an introducer needle for left handed use, the introducer needle would be rotated 180 degrees with respect to the grip component from what is shown in FIGS. 1, 1A, 2, and 2A thereby causing the winged grip to extend to the left when the beveled distal tip is facing upward.

Figure 3:
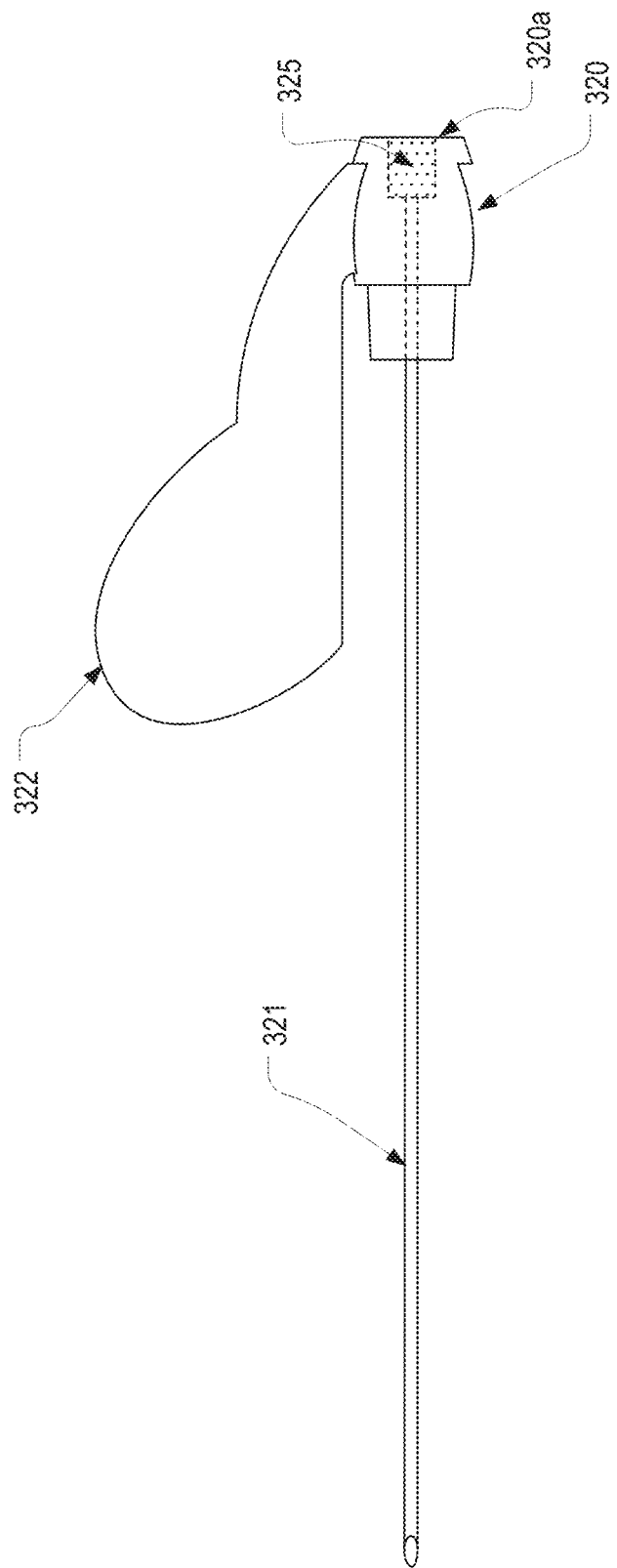
FIG. 3 is a top view of an example introducer needle that includes a grip component forming a winged grip and that also includes a vent for venting gases from within the introducer needle.

FIG. 3 illustrates an example introducer needle 321 that includes a grip component 320 forming a winged grip 322. Grip component 320 includes a vent 320a for venting gases from within introducer needle 321. For example, vent 320a can be formed by incorporating a material 325 within grip component 320 that is permeable to gas but not to fluids. Although not shown, vent 320a may alternatively be formed as one or more openings within grip component 320 that are sufficiently large to allow the passage of gas, but that are sufficiently small to prevent or minimize the flow of fluids through the openings. Accordingly, any type of vent that can be formed within grip component 320 for venting gases from within introducer needle 321 can be employed in embodiments of the present invention.

A grip component of an introducer needle can be configured with a vent to facilitate flow of blood into the introducer needle. This flow of blood, or flashback, can provide visual feedback to the clinician that the introducer needle has been properly placed within the vasculature of the patient. Although not shown in FIG. 3, an introducer needle in accordance with one or more embodiments of the invention can include a notch or opening to allow the blood to flow into the catheter where it will be visible as flashback.

Figure 4A:
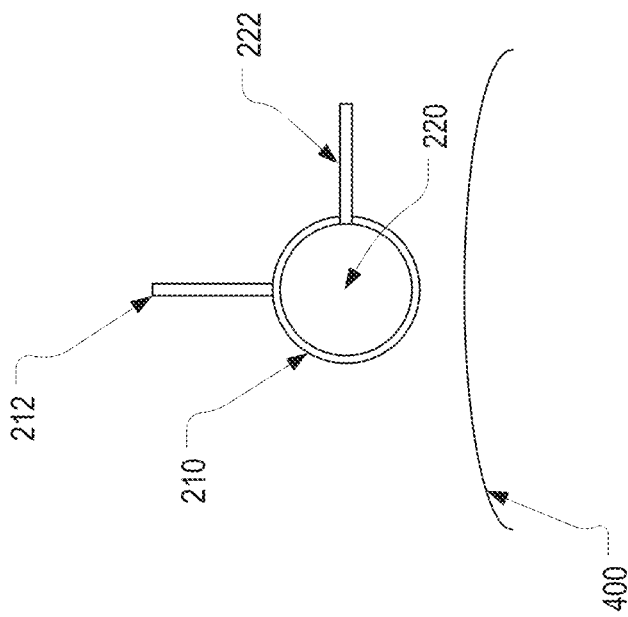
FIGS. 4A and 4B are proximal views of the example PIVC of FIG. 2 showing different rotational positions between the grip component and the catheter adapter.
Figure 4B:
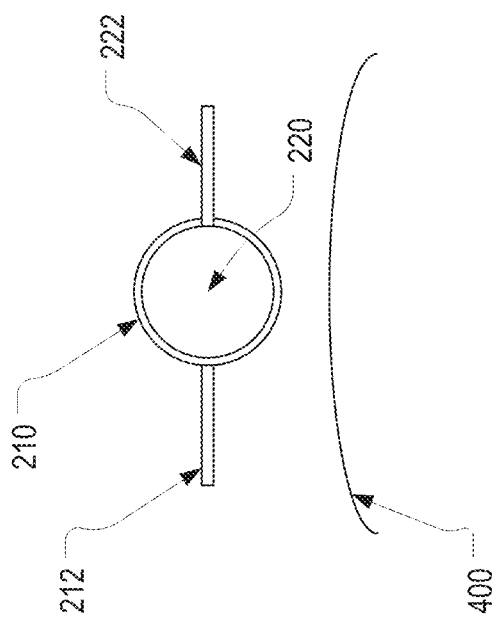

FIGS. 4A and 4B are proximal views of PIVC 200 when positioned over a patient's arm 400 prior to or during insertion of introducer needle 211 into the patient's vasculature. FIG. 4A represents a first relative positioning between catheter adapter 220 and grip component 210 (or equally between catheter adapter 220 and introducer needle 211), while FIG. 4B represents a second relative positioning between catheter adapter 220 and grip component 210. As described above, in some embodiments, winged grip 222 can be aligned with the bevel of the distal tip of introducer needle 211. In such cases, the orientation of winged grip 222 shown in both FIGS. 4A and 4B would result in the bevel facing upward.

Because grip component 220, in some embodiments, can be rotatable within catheter 210, winged grip 212 can be repositioned with respect to winged grip 222. Some clinicians may prefer having winged grips 212 and 222 spaced 180 degrees apart as is shown in FIG. 4A, while others may prefer having winged grips 212 and 222 spaced 90 degrees apart as shown in FIG. 4B. Grip component 220, and more particularly distal portion 223, can be configured to allow this type of rotation so that winged grips 212 and 222 can be positioned in accordance with a particular clinician's preferences.

In some embodiments, grip component 220 and/or catheter adapter 210 can include one or more structures for limiting the relative rotation between the two components. For example, as shown in FIGS. 4C and 4D, catheter adapter 210 can include protrusions 401a and 401b that are configured to contact winged grip 222 to limit rotation to 90 degrees. As shown in FIG. 4C, protrusion 401b is positioned on an external surface of catheter adapter 210 (e.g. near the proximal opening) so that when winged grip 212 is rotated away from winged grip 222, protrusion 401b contacts a bottom surface of winged grip 222 stopping rotation once the two components are positioned 180 degrees apart. Similarly, as shown in FIG. 4D, protrusion 401a is positioned on an external surface of catheter adapter 210 so that when winged grip 212 is rotated towards winged grip 222, protrusion 401a contacts a top surface of winged grip 222 stopping rotation once the two components are positioned 90 degrees apart.

Protrusions 401a and 401b could also be located to enable different ranges of motion from what is shown in FIGS. 4C and 4D. In other embodiments, one or more protrusions or other structures could be formed on grip component 220 so as to contact one or more other suitable structures formed on catheter adapter 210 to limit rotation to a desired amount.

In some embodiments of the present invention, the catheter adapter (e.g. catheter adapters 110, 210, 510, 610) can be colored based on a gauge of the catheter. In this way, a clinician can quickly and easily identify a PIVC of a desired gauge by simply locating a PIVC having a catheter adapter of the appropriate color. Similarly, the clinician can quickly identify the gauge of a particular PIVC using the color of its catheter adapter.

Figure 5:
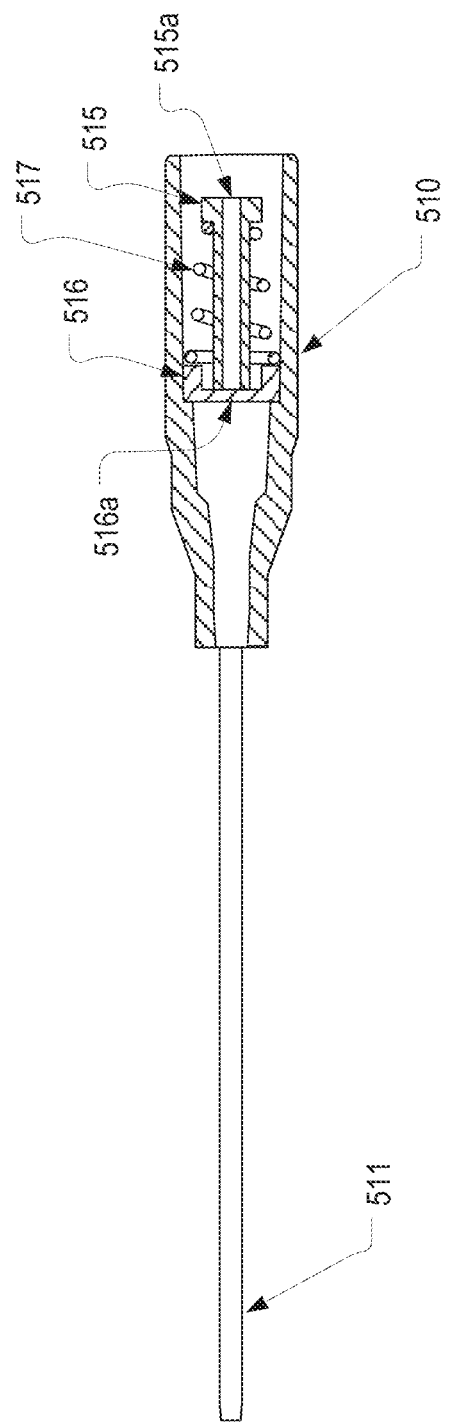
FIG. 5 is a cross-sectional top view of an catheter adapter having a blood-control feature that can be used in a PIVC configured in accordance with one or more embodiments of the present invention.

In some embodiments of the present invention, the catheter adapter of a PIVC can include a blood-control feature. For example, FIG. 5 illustrates a cross-sectional view of a catheter adapter 510 that includes a blood-control feature. The blood-control feature is implemented using an elastomeric valve or septum 516 and an activator 515. Activator 515 includes a lumen 515a through which an introducer needle can extend. Septum 516 can include a slit 516a through which the introducer needle as well as activator 515 can extend.

FIG. 5 can represent the state of the blood-control feature when a device is not connected to catheter adapter 510. As shown, when no device is connected, activator 515 is positioned proximally to septum 516. Septum 516 thereby forms a seal preventing fluid from flowing through catheter adapter 510. In some embodiments, including as shown in FIG. 5, the blood-control feature can include a spring 517 for biasing activator 515 in the proximal position.

Once a device is connected to catheter adapter 510, the device can force activator 515 into a distal position through septum 516 thereby opening a fluid path through septum 516. Then, once the device is disconnected from catheter adapter 510, spring 517 can force activator 515 back into the proximal position again allowing septum 516 to form a seal. In some embodiments, septum 516 and/or activator 515 can be configured to naturally bias activator 515 into the proximal position such that spring 517 would not be required.

Accordingly, embodiments of the present invention provide a non-integrated PIVC having a winged grip and incorporating a blood-control feature. Such PIVCs can be employed to perform intravenous access in a similar manner as with prior art winged infusion sets, but without the many limitations inherent in such prior art sets. Further, because a PIVC in accordance with embodiments of the invention can allow the winged grips to be rotated with respect to one another, a greater degree of customization can be provided to match the preferences of a particular clinician.

Figure 6A:
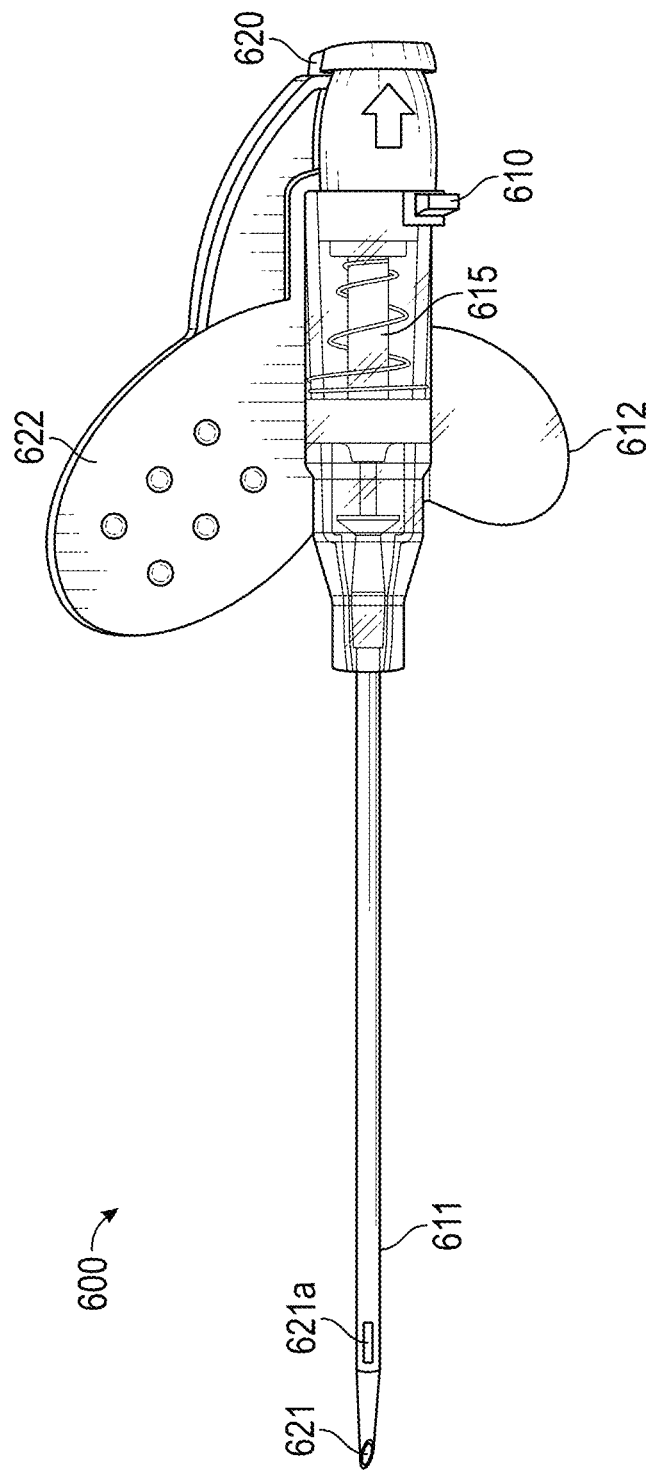
FIG. 6A is a perspective view of an example PIVC configured in accordance with one or more embodiments of the present invention.

FIG. 6A illustrates a top perspective view of a PIVC 600 that is configured in accordance with one or more embodiments of the present invention. PIVC 600 includes a catheter adapter 610 that includes a catheter 611 and forms a winged grip 612. PIVC 600 also includes an introducer needle 621 that includes a grip component 620. The grip component 620 extends to form a winged grip 622. Introducer needle 621 includes a notch 621a to facilitate the appearance of flashback during insertion. Although not shown, grip component 620 can include a vent for venting gases from within introducer needle 621 thereby facilitating blood flow into introducer needle 621 and through notch 621a. PIVC 600 also includes a blood-control feature 615 similar to the blood control feature described with reference to FIG. 5.

Figure 6B:
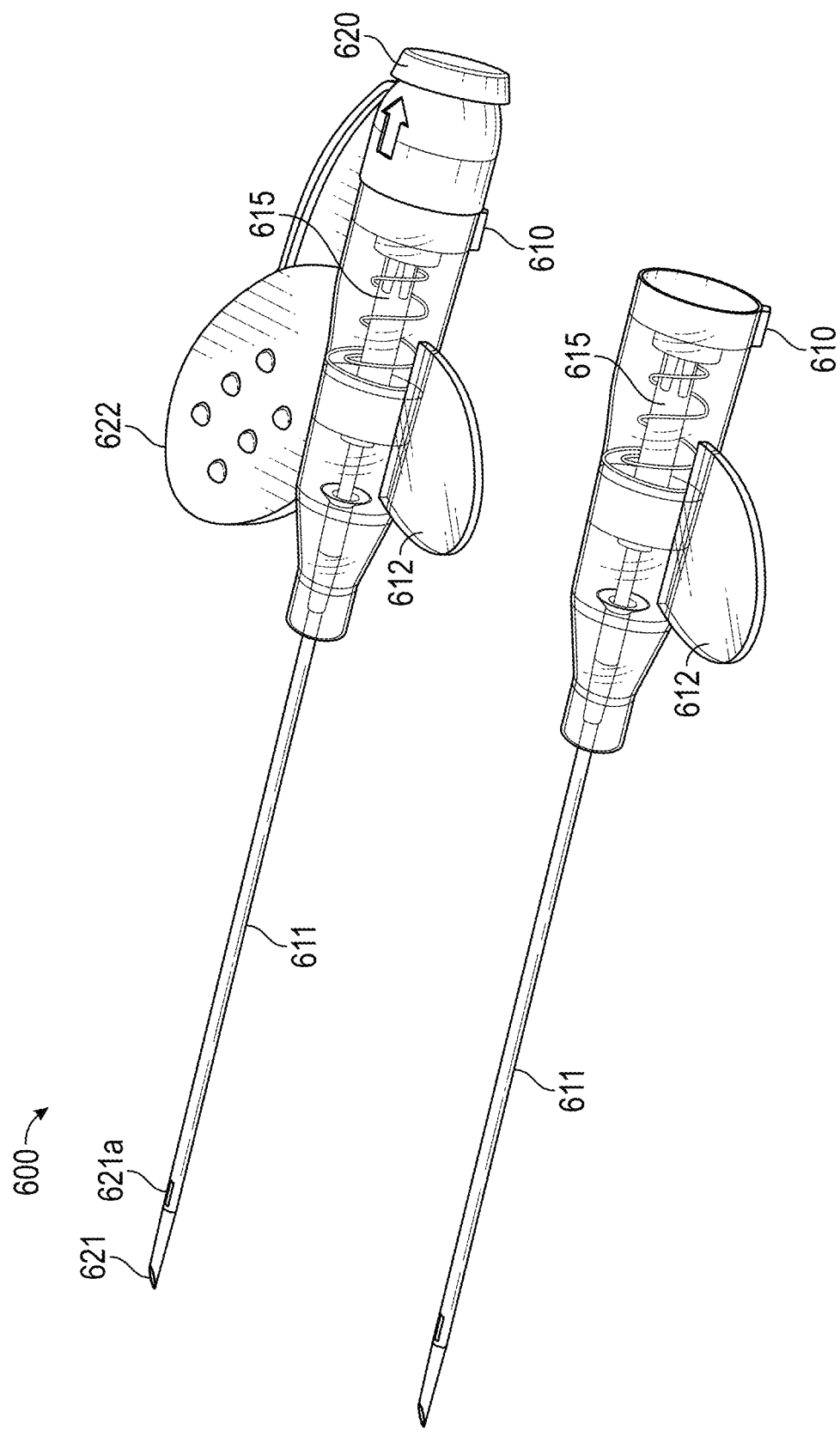
FIG. 6B is a perspective view of two example PIVCs illustrating the introducer needle both positioned within and removed from the catheter adapter.
Figure 7:
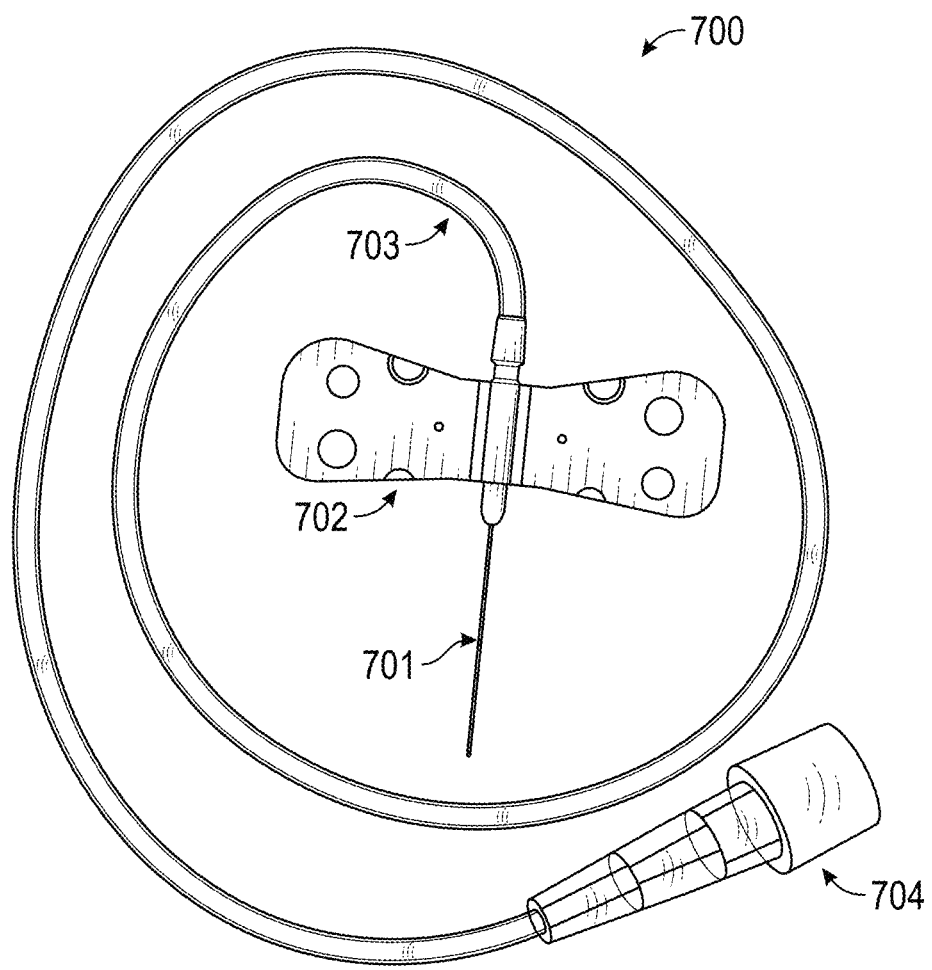
FIG. 7 is a top perspective view of a prior art winged infusion set.

FIG. 6B provides a front perspective view of PIVC 600 when introducer needle 621 is contained within catheter adapter 610 (top) and when introducer needle 621 has been removed from catheter adapter 610 (bottom). As shown, once introducer needle 621 is removed, blood-control feature 615 can form a seal preventing the flow of blood through catheter adapter 610. With introducer needle 621 removed, a device can be attached to the proximal end of catheter adapter 610. The device can be shaped so that, when attached, it activates blood-control feature 615 (e.g. by forcing an activator through a septum or otherwise opening a valve) thereby allowing the flow of fluids through catheter adapter 610.

Many variations of the above described examples may also be employed on a PIVC configured in accordance with the present invention. For example, in addition to the shapes of the winged grips shown in the figures, other shapes of winged grips can also be used. In embodiments that employ a winged grip on the catheter adapter, the opposing winged grips need not have symmetrical shapes. For example, one winged grip can be rounded (such as is shown in the figures) while the other may be straight.

Additionally, in any of the above described examples, a needle shield may be employed to cover the beveled distal tip of the introducer needle once the introducer needle is withdrawn from the catheter. Also, in any of the above described examples, an antimicrobial coating can be applied within the catheter adapter including on any blood-control feature.

In some embodiments, a PIVC can include an integrated extension set. For example, an extension set can be integrated into the proximal side of the catheter adapter. In such cases, a blood-control feature may not be required since the integrated extension set with adapter can serve as the blood control feature and access port. In this case, a septum in the catheter adapter can provide a non-opening seal once the introducer needle is withdrawn.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A peripheral intravenous catheter comprising:
a catheter adapter comprising a first protrusion formed on an outer surface of the catheter adapter, and a second protrusion formed on the outer surface of the catheter adapter spaced apart from the first protrusion, wherein the catheter adapter further comprises a catheter adapter winged grip;
a catheter extending distally from the catheter adapter; and
an introducer needle that inserts through the catheter and comprises a distal end having a bevel, the introducer needle having a grip component at proximal end of the introducer needle, the grip component configured to be inserted into the catheter adapter to secure the introducer needle to the catheter adapter, the grip component extending outwardly and distally to form an introducer needle winged grip that extends along the outer surface of the catheter adapter between the first and second protrusions when the grip component is inserted into the catheter adapter, wherein a portion of the introducer needle winged grip extends outwardly and away from a longitudinal axis of the peripheral intravenous catheter,
wherein when the grip component is in an insertion configuration ready for insertion into a patient:
the bevel of the introducer needle is facing directly upward and a central axis of the bevel divides the peripheral intrvenous catheter into a right side and a left side;
the introducer needle winged grip is disposed on the right side of the of the peripheral intravenous catheter and proximate the first protrusion; and
the catheter adapter winged grip is on the left side of the peripheral intravenous catheter directly across from the introducer needle winged grip and the second protrusion is disposed between the introducer needle winged grip and the catheter adapter winged grip, wherein the catheter adapter is configured to rotate with respect to the grip component from the insertion configuration to a second position, wherein when the catheter adapter is in the second position, the catheter adapter winged grip is rotated towards the introducer needle winged grip compred to the first position, and the second protrusion contacts a top of the introducer needle winged grip to limit rotation of the catheter adapter.

2. The peripheral intravenous catheter of claim 1, wherein the catheter adapter is colored based on a gauge of the catheter.

3. The peripheral intravenous catheter of claim 1, wherein the introducer needle includes a needle shield for shielding a tip of the introducer needle.

4. The peripheral intravenous catheter of claim 1, wherein the first protrusion and the second protrusion are spaced apart such that catheter adapter is configured to rotate at least 90 degrees between the first position and the second position.

5. The peripheral intravenous catheter of claim 1, wherein the first protrusion and the second protrusion are spaced apart such that catheter adapter is configured to rotate 90 degrees between the first position and the second position.

* * * * *